United States Patent [19]
Faul et al.

[11] Patent Number: 5,287,845
[45] Date of Patent: Feb. 22, 1994

[54] ENDOSCOPE FOR TRANSURETHRAL SURGERY

[75] Inventors: Peter Faul, Memmingen; Heinz Hluchy; Armin Schlüter, both of Hamburg, Fed. Rep. of Germany

[73] Assignee: Olympus Winter & Ibe Gmbh, Hamburg, Fed. Rep. of Germany

[21] Appl. No.: 820,926

[22] Filed: Jan. 15, 1992

[30] Foreign Application Priority Data

Jan. 19, 1991 [DE] Fed. Rep. of Germany ....... 4101472

[51] Int. Cl.$^5$ ................................................. A61B 1/30
[52] U.S. Cl. ............................................ 128/7; 128/4; 606/46
[58] Field of Search ................. 128/3, 4, 6, 7, 20, 128/17, 10; 604/22, 264, 164; 606/46, 47, 45

[56] References Cited

U.S. PATENT DOCUMENTS

| 2,448,741 | 9/1948 | Scott et al. | |
| 2,487,502 | 11/1949 | Willinsky | |
| 3,144,020 | 8/1964 | Zingale | 606/46 X |
| 4,132,227 | 1/1979 | Ibe | 128/7 X |
| 4,567,880 | 2/1986 | Goodman | 128/7 |
| 4,765,314 | 8/1988 | Kolditz et al. | 128/4 |
| 4,819,620 | 4/1989 | Okutsu | 128/4 |
| 4,904,246 | 2/1990 | Atkinson | 604/167 X |
| 5,184,602 | 2/1993 | Anapliotis et al. | 128/4 X |

FOREIGN PATENT DOCUMENTS

| 935391 | 11/1955 | Fed. Rep. of Germany . | |
| 7426959 | 8/1974 | Fed. Rep. of Germany . | |
| 2803897 | 8/1979 | Fed. Rep. of Germany | 128/4 |
| 2915271 | 10/1980 | Fed. Rep. of Germany | 128/4 |
| 3615694 | 11/1987 | Fed. Rep. of Germany | 128/4 |
| 0759088 | 9/1980 | U.S.S.R. | 128/4 |
| 1391611 | 4/1988 | U.S.S.R. | 128/4 |

Primary Examiner—Richard J. Apley
Assistant Examiner—Karen A. Jalbert
Attorney, Agent, or Firm—Walter C. Farley

[57] ABSTRACT

An endoscope for transurethral surgery and has a main body irrotationally supporting an optics and a surgical instrument, further an outer tube affixed to the main body and tubularly enclosing the optics and the surgical instrument, which is characterized in that the outer tube is rotational relative to the remaining endoscope parts.

5 Claims, 4 Drawing Sheets

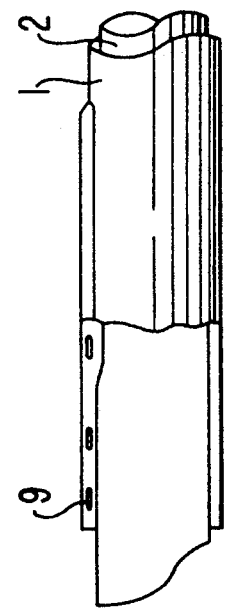
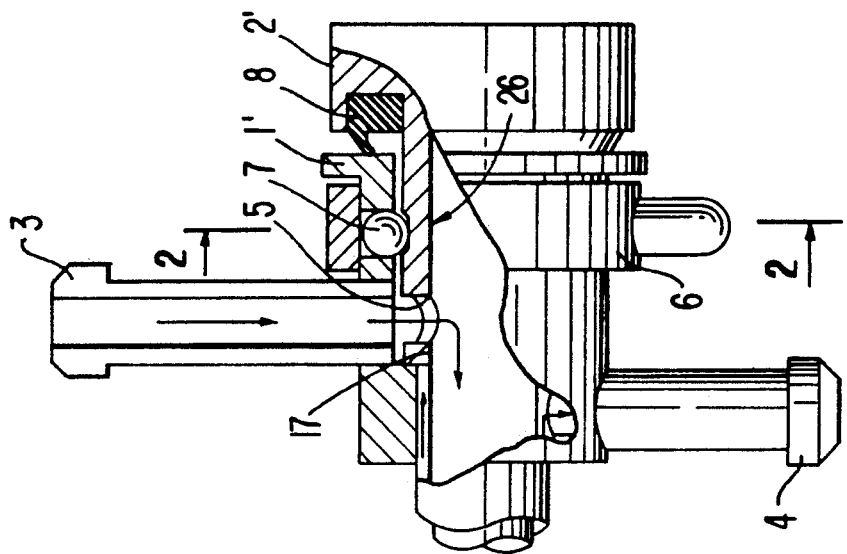
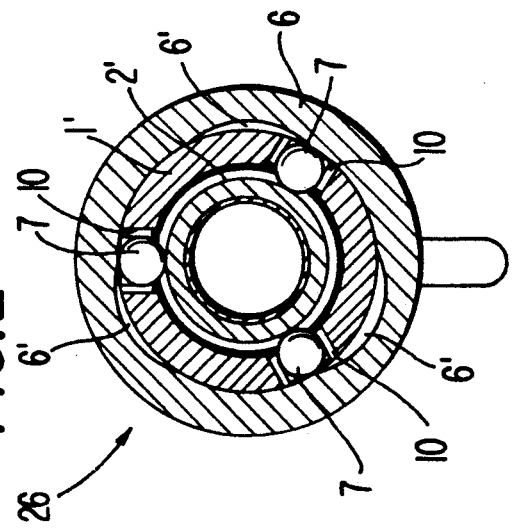

ENDOSCOPE FOR TRANSURETHRAL SURGERY

FIELD OF THE INVENTION

This invention concerns an endoscope for transurethral surgery having an optical system.

BACKGROUND OF THE INVENTION

Endoscopes used for such surgery have outer tubes which are placed into the patient's urethra. The optical system allows viewing the field of surgery. The surgical instrument, for instance scissors, tongs or, typically, a high-frequency cutting electrode, allows surgery, specifically, cutting. The main body of the endoscope comprises actuators driving the surgical instrument, for instance to reciprocate it axially. As a rule, the endoscope also comprises fittings for flushing water with which the area of surgery is flushed to achieve better viewing.

As regards endoscopes comprising a pistol grip at the main body, rotating means are known whereby parts of the main body can be rotated relative to the remaining parts of the endoscope. However, the surgical instrument and the outer tube always are mutually non-rotational.

When operating in the bladder, in particular when resecting the prostate gland, the rotational position of the surgical instrument relative to field of surgery frequently must be changed. Illustratively, when operating on the prostate, removal must take place alternatingly on the right, left, top and bottom. When using a known endoscope of the kind mentioned above wherein the surgical instrument is stationary relative to the outer tube, this outer tube therefore must be constantly rotated in the urethra. However, the friction between the outer tube wall and the urethra wall irritates the sensitive mucous lining of the urethra and may lead to injury.

SUMMARY OF THE INVENTION

An object of the present invention is provide an endoscope of the initially cited kind in which these stresses on and injuries to the patient will be avoided.

Briefly described, the invention comprises an endoscope for transurethral surgery including a main body nonrotatably attached to and supporting an optical system and a surgical instrument. An outer tube is coupled to the main body and tubularly encloses the optical system and the surgical instrument, the outer tube being rotatably mounted relative to the main body, the optical system and also the surgical instrument.

In an endoscope in accordance with the invention, because the outer tube and the remaining endoscope parts are relatively rotatable, when rotating the surgical instrument into position for a new direction of operation, the outer tube remains at rest in the urethra. The above mentioned irritations to and injuries of the urethra are entirely avoided.

Providing the endoscope with an inner tube which is not rotatable relative to the main body permits one to provide a complete endoscope with its tube onto which the rotationally linked outer tube is attached as an accessory. Such an instrument may be used with or without the outer tube. Upon removal of the outer tube, there remains an autonomous endoscope with tube. Also, retrofitting an outer tube onto a conventional endoscope is possible, and illustratively it may be attached as a plain tubular sleeve in the absence of special coupling means.

It is advantageous to provide an endoscope with two ducts for liquids, making possible constant flushing of the area of surgery while retaining the advantages of the rotatable outer tube.

Attaching a feed fitting to the outer tube is advantageous since it will always be fixed in position and the feed hose is prevented from twisting.

Rotatably mounting a feed fitting to the inner tube offers the advantage that, as needed, the inner tube can be used alone as the tube for intermittent flushing with its rotary flushing fitting. If the outer tube is rigidly coupled to the rotary flushing fitting of the inner tube, then both the feed and the drain fittings are fixed in position relative to the outer tube, and the inner tube is rotatably relative to the outer tube.

Because for cleaning and sterilization the outer and inner tubes advantageously shall be separate, locking between the inner and outer tubes is provided as a rule. Advantageously, in accordance with the invention, the locking means simultaneously serves as a rotary bearing for the inner tube. This design is compact and allows easy handling.

An O-ring is used as the seal in the rotary flushing fitting of a known tube with intermittent flushing (no outer tube). If such an O-ring were used as seal in the endoscope of the invention between the outer and inner tubes, the friction between the inner and outer tubes would be larger than the friction between the outer tube and the urethra, whereby undesired co-rotation and hence friction between the outer tube and the urethra might ensue. For this reason, using a low-friction lip seal is advantageous as a seal between the inner and outer tubes.

BRIEF DESCRIPTION OF THE DRAWINGS

A preferred embodiment of the invention is shown in illustrative and schematic manner in the drawing, in which:

FIG. 1 is a foreshortened side elevation in partial section of a first embodiment of an endoscope of the invention;

FIG. 2 is a transverse sectional view of the endoscope of FIG. 1 along line 2—2;

DESCRIPTION OF THE PREFERRED EMBODIMENT

Figure 3:
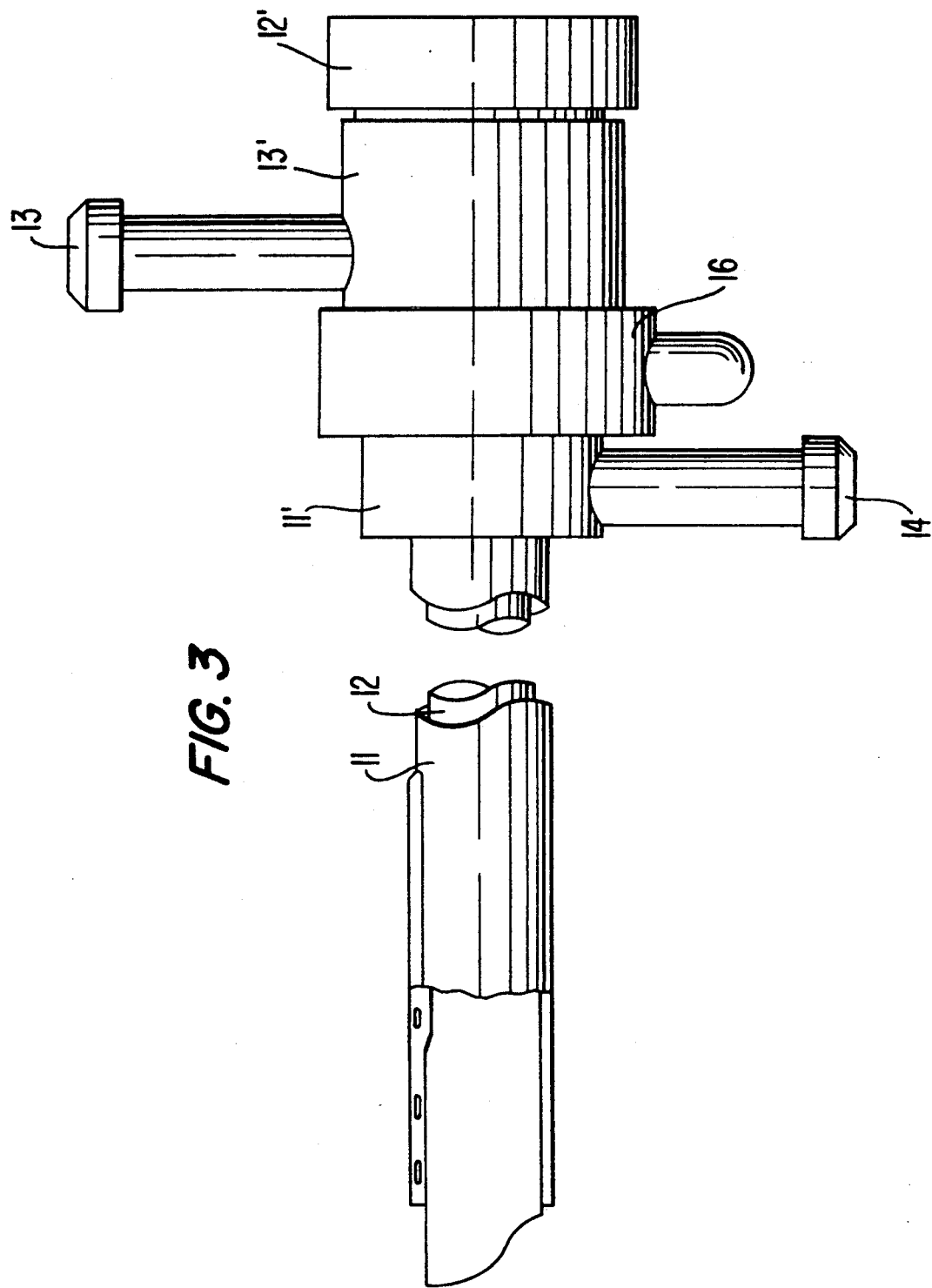
FIG. 3 is a foreshortened side elevation of a further embodiment of the invention with a rotary feed fitting at the inner tube.

FIG. 1 shows a first embodiment of the endoscope of the invention, without optics and without instrument support, which includes an outer tube 1 and an inserted inner tube 2. The outer tube 1 becomes thicker at its proximal end to form a housing 1' and the inner tube 2 becomes thicker to form a seal 2'. A feed fitting 3 and a drain fitting 4 are rigidly affixed to the housing 1'. Flushing liquid is supplied through the feed fitting when surgery is being performed. The flushing liquid passes through one or more boreholes 5 in an annular duct of the seal 2' into the duct of the inner tube 2 and can discharge from the distal end of this tube 2. The flushing liquid is evacuated through boreholes 9 and through a duct formed by the gap between the outer tube 1 and the inner tube 2 and through the discharge fitting 4.

Figure 4:
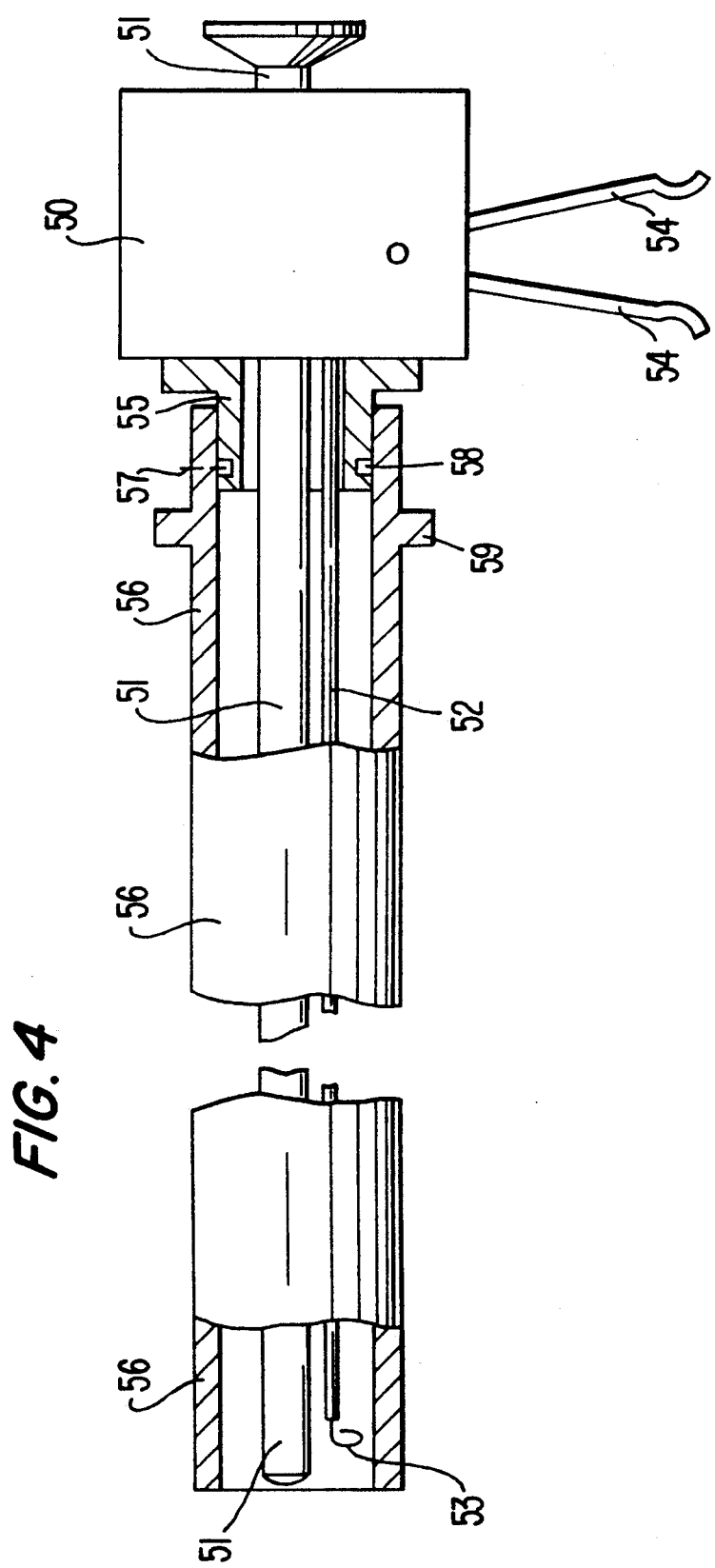
FIGS. 4 through 6 are highly schematic longitudinal sectional views of three further embodiments of the endoscope of the invention.

The tube arrangement shown in FIG. 1 can be attached by the housing 2' to the main body of an endoscope, not shown, for instance to the fitting flange 55 of an endoscope of the type shown in FIG. 4.

The housing 2' of the inner tube 2 is rotatably linked by a lock 26 to the housing 1' of the outer tube 1. The housing 1' also serves as the race of a ball bearing of which the balls 7 run in an annular groove of the housing 2', whereby axial displacement between the inner tube 2 and the outer tube 1 is prevented. A low-friction lip-seal 8 is used as a seal between the housings 1' and 2'.

When resecting, the inner tube 2, including the surgical instrument and optics (which are not shown), can be rotated about its longitudinal axis, whereas the outer tube 1 advantageously may remain in position, so that friction between the outer tube and the urethra on account of endoscope rotation practically does not occur. The friction caused by the lip seal is less than that between the outer tube and the urethra and thereby rotation of the outer tube 1, even when not manually fixed in position by the surgeon, is avoided. Because the outer tube 1 no longer rotates, the structure concurrently has the further advantage that the undesired twisting of the hoses connected to it and serving to supply and drain the liquid is eliminated. A constriction 17 is provided to seal between the outer and inner tubes 1 and 2 respectively, as a result of which a flow bypass between feed and drain ducts is kept low. If the flow bypass must be avoided entirely, a seal, preferably a low-friction lip seal can be provided.

The section shown in FIG. 2 represents the lock 26 of the endoscope of FIG. 1 when in the locked position. The lock 26 fixes the mutual axial positions of the outer and inner tubes 1 and 2 and simultaneously serves as a pivot bearing. The balls 7 are retained by ball containers 10 in the housing 1' which thereby serve as the ball-bearing race. In the locked position, the balls 7 run in an annular groove of the housing 2' of the inner tube 2. By clockwise rotation of the locking ring 6 (as seen in FIG. 2), the balls 7 are released by alignment of the balls with recesses 6' so that the balls can move radially, allowing relative movement between the tubes in the axial direction and the inner tube 2 can be withdrawn from the outer tube 1.

FIG. 3 shows a variation of an endoscope comprising an outer tube 11 with a fixed drain fitting 14 and of an inner tube 12 with a feed fitting 13 mounted to the rotary ring 13'. The outer tube 11 is thicker at its proximal end to form a housing 11' with a drain fitting 14 and a locking ring 16. The inner tube 12 is thicker at its proximal end to form a housing 12' adjacent the feed fitting 13 which is rotatable by means of the rotary ring 13'. The inner tube 12 is telescoped into the outer tube 11 and the rotary ring 13' is solidly locked by the locking ring 16 to the housing 11' of the outer tube 11.

For purposes of resection, the inner tube 12, together with the housing 12', can be rotated about its axis, whereas the outer tube 11 together with the drain fitting 14 and coupled rotary ring 13' and feed fitting 13 can remain in position, so that, in this embodiment also, the friction of rotation between the urethra and the outer tube 11 and the disadvantageous twisting of the connected hoses is eliminated. As compared to the embodiment of FIG. 1, the FIG. 3 embodiment offers the further advantage that the endoscope can be used without outer tube 11 as needed with intermittent flushing and rotary feed fitting 13.

In highly diagrammatical form, FIG. 4 shows another embodiment of the endoscope of the invention. Contrary to the embodiment of FIGS. 1 through 3, the entire endoscope is shown with a main body 50 housing an exchangeable optical system 51. A surgical instrument for this embodiment is shown as an elongated support 52 for a high-frequency power driven cutting loop 53. This loop is moved axially by levers 54 mounted on the main body 50 which are actuated like scissors. A much simplified connecting flange 55 is present at the main body and supports an easily rotatable outer tube 56. A pin 57, which for instance may be threaded and removable, axially secures the outer tube 56 in an annular groove 58 of the connecting flange 55.

When this instrument is placed by means of the outer tube 56 into the urethra of a patient (not shown), then, upon actuating the levers 54, the loop 53 may be advanced to the surgical area located in front of the distal end of outer tube 56. If surgery should then need to proceed in another angular position, with the outer tube 56 remaining firmly in place in the urethra, the main part 50 with the optics 51 and surgical instrument 52 can be rotated.

No inner tube is provided in this simple and economical instrument. However, a liquid fitting (not shown) to feed and drain the liquid to and from the inside of the outer tube 56 may be provided. An outwardly projecting flange 59 is present at the outer tube 56 and illustratively may comprise external flutings and may be used to hold the outer tube while the remainder of the endoscope is being rotated.

Figure 5:
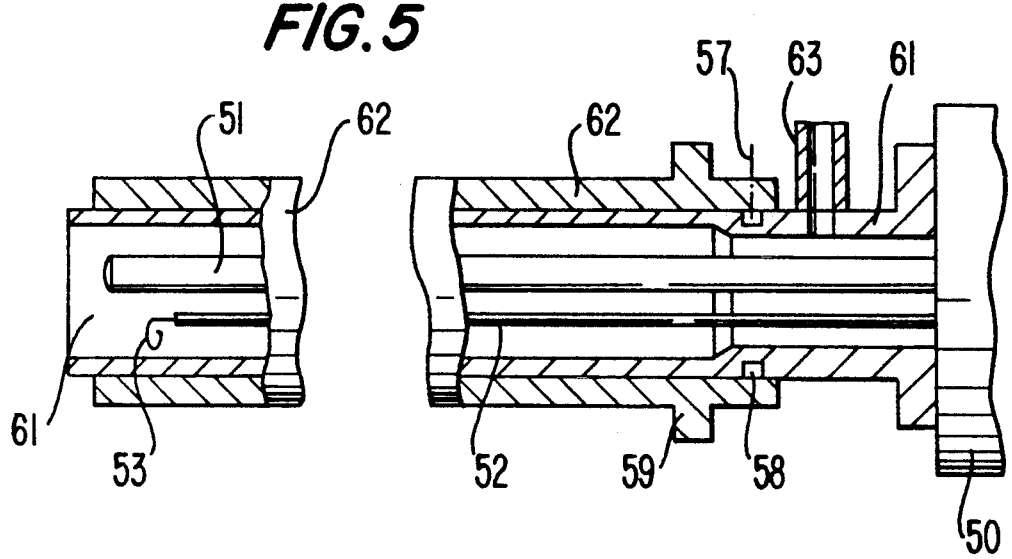

FIG. 5 shows another embodiment in a view similar to FIG. 4. The main body 50, optics 51 and surgical instrument 52 are precisely the same as in FIG. 4. The connecting flange 55 in this arrangement is, however, part of an inner tube 61 enclosing the optics 51 and the surgical instrument 52 over the entire length.

An outer tube 62 in the form of a rotatable, slipped-on sleeve is present on the inner tube 61 and is secured against relative axial movement by the pin 57 and the groove 58 in the manner shown by FIG. 4. In the embodiment of FIG. 5, a liquid inlet fitting 63 is present at the free, proximal end of the inner tube 61.

Figure 6:
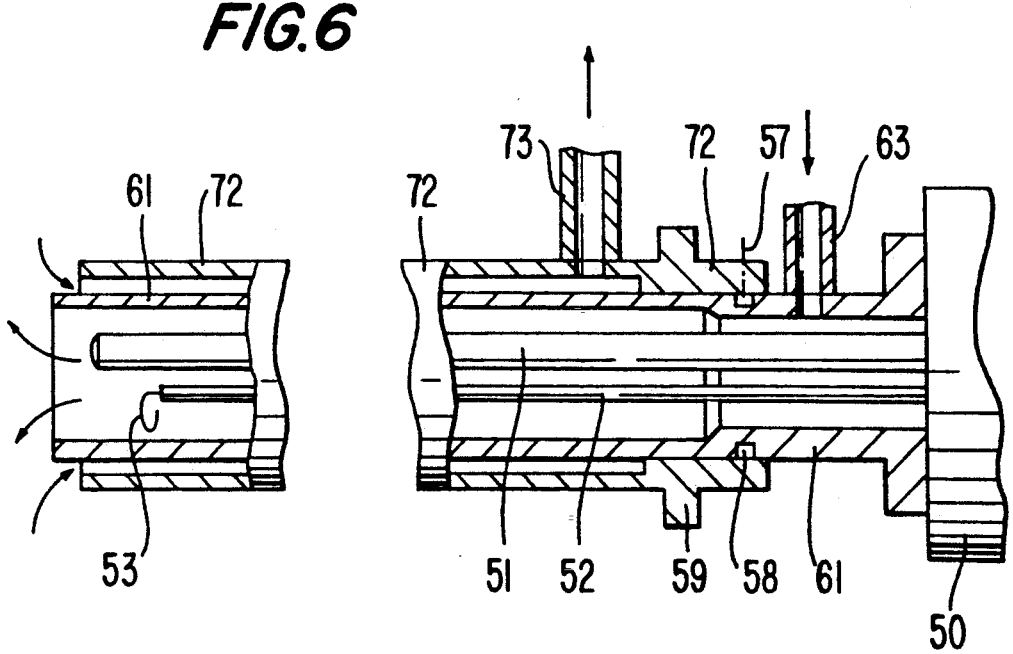

FIG. 6 shows another embodiment in a view similar to FIG. 5. In this embodiment, the main body 50, optics 51, surgical instrument 52 and the entire inner tube 61 coincide with the embodiment of FIG. 5.

In this embodiment the outer tube 72 is supported and secured at its proximal end zone by the pin 57 and groove 58 on the inner tube 61 in the same manner as shown in FIG. 5. However, the outer tube 72 comprises over its substantial distal zone an inside diameter which is larger than the outside diameter of the inner tube 61. Accordingly a conduit for liquid is created between the tubes 61 and 72 and can be connected by means of a second liquid fitting 73.

As shown by the Figure, liquid may be supplied through the liquid fitting 63 and be drained through the liquid fitting 73 in the manner shown at the distal end of the endoscope of FIG. 6.

The embodiments of FIGS. 4 through 6 are highly schematic. A number of desirable or advantageous details have been omitted for the sake of clarity in the drawings. Illustratively, required seals which serve to seal the outer tube at the proximal end have been omitted. Also omitted is the easy removal of the outer tube using, advantageously, a simple quick-disconnect means in the manner shown by FIGS. 1 through 3. Again omitted from the Figures is the possibility of detachability of the inner tube 6 in the manner shown by FIGS. 1 through 3.

Considering now the embodiment of FIG. 6, it will be noted that the drain fitting 73 is fixed relative the outer tube 72. As the outer tube 72 always is stationary relative to the patient and will not be rotated, the drain fitting 73 also shall always remain in the same position.

However, the feed fitting 63 is constantly being rotated because it is attached to the inner tube 61. Therefore, hoses starting from the feed fitting always must be rotated to-and-fro when the instrument is being rotated. It follows that the arrangement of FIG. 1 is advantageous, because it calls for the feed fitting 3 being rigidly affixed to the outer tube 1 while nevertheless the liquid appropriately is connected to and passes through the inside of the inner tube 2. In the embodiment of FIG. 1, both the feed fitting 3 and the drain fitting 4 always remain in the same position, irrespective of the rotation of the remainder of the endoscope.

We claim:

1. An endoscope for transurethral surgery comprising
a main body nonrotatably attached to and supporting an optical system and a surgical instrument;
an outer tube coupled to said main body and tubularly enclosing said optical system and said surgical instrument,
an inner tube inside of said outer tube and enclosing said optics and said surgical instrument, said inner tube being nonrotatably mounted relative to said main body, said optical system and said surgical instrument
said outer tube being rotatably mounted relative to said main body, said optical system and said surgical instrument,
said outer tube having an inside diameter sufficiently larger than the outside diameter of said inner tube to leave a fluid passage therebetween, and
proximal ends of said inner and outer tubes being mutually sealed;
a feed fitting connected to the proximal end of said inner tube to form a feed duct to the interior of said inner tube; and
a drain fitting connected to said fluid passage between said tubes forming a drain duct.

2. An endoscope according to claim 1 wherein said feed fitting is rigidly attached to said outer tube and is permanently connected to allow flow with the feed duct in the inner tube.

3. An endoscope according to claim 1 wherein said feed fitting is rotatably mounted to said inner tube and wherein said outer tube can be coupled to the feed fitting.

4. An endoscope according to claim 1 and further comprising locking means between said inner and outer tubes for locking said tubes against relative axial motion, said locking means also comprising a rotation bearing.

5. An endoscope according to claim 1 and including at least one lip seal mounted between said inner tube and said outer tube in order to mutually seal said tubes.

* * * * *